United States Patent

Cohen et al.

[11] 4,018,798
[45] Apr. 19, 1977

[54] SUBSTITUTED (4-OXO-4H-1-BENZOPYRAN-2-YL)CYCLOPROPANE CARBOXYLIC ACIDS AND ESTERS

[75] Inventors: Marvin P. Cohen, New Milford; John Shavel, Jr., Mendham; Max Von Strandtmann, Rockaway Township, all of N.J.

[73] Assignee: Warner-Lambert Company, Morris Plains, N.J.

[22] Filed: Nov. 20, 1975

[21] Appl. No.: 633,745

[52] U.S. Cl. .................. 260/345.2; 260/345.5; 424/283
[51] Int. Cl.² .................. C07D 311/02
[58] Field of Search .................. 260/345.2, 345.5

[56] References Cited

UNITED STATES PATENTS

| 3,823,165 | 7/1974 | Cairns et al. | 260/345.2 |
| 3,853,921 | 12/1974 | Klutchko et al. | 260/345.2 |
| 3,948,955 | 4/1976 | Lee et al. | 260/345.2 |

FOREIGN PATENTS OR APPLICATIONS

| 815,896 | 4/1974 | Belgium | 260/345.2 |

Primary Examiner—Bernard Helfin
Assistant Examiner—Nicky Chan
Attorney, Agent, or Firm—Albert H. Graddis; Frank S. Chow

[57] ABSTRACT

The present invention relates to substituted [4-oxo-4H-1-benzopyran-2-yl]cyclopropane carboxylic acids and esters having the following structural formula:

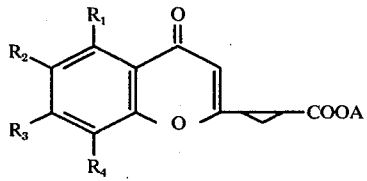

wherein $R_1$, $R_2$, $R_3$ and $R_4$ are hydrogen, alkyl, lower alkoxy, phenyl or when $R_1$ and $R_2$ are hydrogen, $R_3$ and $R_4$ taken together form an additional aromatic ring and A is hydrogen or ethyl. The compounds of this invention exhibit anti-allergy properties and are indicated in the management of allergic manifestations such as bronchial asthma.

7 Claims, No Drawings

SUBSTITUTED (4-OXO-4H-1-BENZOPYRAN-2-YL)CYCLOPROPANE CARBOXYLIC ACIDS AND ESTERS

The present invention relates to substituted [4-oxo-4H-1-benzopyran-2-yl]cyclopropane carboxylic acids and esters having the following structural formula:

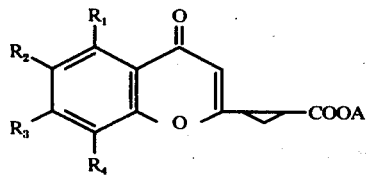

wherein $R_1$, $R_2$, $R_3$ and $R_4$ are hydrogen, lower alkyl, lower alkoxy or phenyl or when $R_1$ and $R_2$ are hydrogen, $R_3$ and $R_4$ taken together form an additional aromatic ring.

In the above definitions for $R_1$, $R_2$, $R_3$ and $R_4$, lower alkyl and the lower alkyl portion of lower alkoxy are meant to embrace straight- or branched-chain alkyl radicals of 1–6 carbon atoms, for example, methyl, ethyl, propyl, isopropyl, n-butyl, n-amyl, n-hexyl, ethylbutyl, 2,3-dimethylbutyl, and so on. The term "aromatic ring" denotes a monocyclic aromatic hydrocarbon radical of 6–10 carbon atoms, such as phenyl or tolyl.

The above compounds exhibit anti-allergy properties in mammals. Thus, in tests conducted according to procedures described in I. Mota, *Life Sciences*, 7: 465 (1963) and Z. Ovary, O. Bier, *Proc. Soc. Exptl. Biol. Med.*, 81: 584 (1952), they were found to prevent allergic and asthmatic reactions in rats at dosage levels of about 25 mg/kg intraperitoneally. These compounds are, therefore, indicated in the management of bronchial asthma, hay fever and other similar allergic conditions.

The compounds of the present invention can be administered orally and by such compositions as tablets, pills, dispersible powders and the like. The active ingredient is mixed with at least one inert pharmaceutical diluent such as lactose and suitable granules, using agents such as water or alcohol, and the resulting granules compressed into tablets utilizing standard tabletting procedures.

Liquid pharmaceutically administerable compositions are prepared by dissolving or suspending the active ingredient in a pharmaceutically acceptable carrier such as water or syrup. In addition, the compounds of this invention can be administered by inhalation therapy in which the compound is formulated by standard aerosol technique.

To treat allergic manifestations the compounds of this invention are typically administered in dosages varying between 10–25 mg per kg of body weight 2 to 3 times daily. The precise dosage regimen can be varied depending on the mode of administration, the condition being treated and the host to whom the administration is being made, by methods well-known to the healing arts.

According to the present invention, Compound I is prepared by treating a compound of the formula:

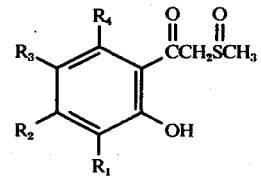

with a compound of the formula:

Generally speaking, this reaction is effected by refluxing together the two starting compound in a suitable solvent such as toluene with a catalytic amount of piperidine. The product formed is recovered from the reaction medium by standard techniques, e.g., crystallization. This reaction yields those compounds of the invention in which A is ethyl. To obtain those compounds in which A is hydrogen, the compound thus obtained is hydrolized in a hot mineral acid, e.g., concentrated sulfuric or hydrochloric acid.

Derivatives of the instant compounds are readily prepared by treating the instant compounds in which A is hydrogen with suitable reagents, e.g., with alcohol to obtain esters, with a base to obtain salts and so on. These derivatives include, for example, the methyl, propyl esters, sodium, potassium, calcium salts and so on.

Starting Compound II is prepared according to the procedure set out in U.S. Pat. No. 3,801,644 and starting Compound III is obtained from commercial sources, e.g., Aldrich Chemical Company.

In order to further illustrate the practice of this invention, the following examples are included:

EXAMPLE 1

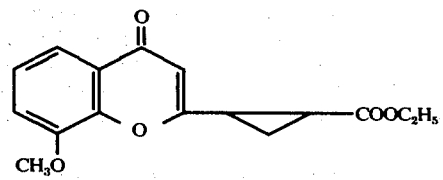

Ethyl 2-(8-methoxy-4-oxo-4H-1-benzopyran-2-yl)cyclopropane carboxylate

A mixture of 11.4g of 2'-hydroxy-3'-methoxy-2-(methylsulfinyl)acetophenone, 7.1g of ethyl 2-formyl-1-cyclopropane carboxylate (Aldrich Chem. Co.), 125ml of toluene and 0.25ml of piperidine were combined and refluxed for 8 hrs. The solution was then chilled, and the crystals that deposited were filtered and recrystallized from absolute ethanol, mp. 141°–44°; yield 6g (46%); λ max mµ (ε) 239 (29,400), 306 (5,250); ν max 730 (m), 1040 (ms), 1130 (m), 1175 (s), 1270 (m), 1580 (s), 1650 (s), 1725 (s) cm$^{-1}$.

Anal. Calcd. for $C_{16}H_{16}O_5$: C, 66.66; H, 5.59. Found: C, 66.74, H, 5.77.

EXAMPLE 2

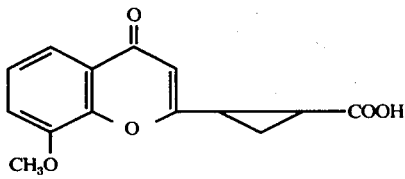

2(8-methoxy-4-oxo-4H-1-benzopyran-2-yl)cyclopropane carboxylic acid

A mixture of 3g of ethyl (8-methoxy-4-oxo-4H-1-benzopyran-2-yl) cyclopropane carboxylate and 25ml of concentrated hydrochloric acid was refluxed for 45 min. The solution was chilled, and the crystalline precipitate that formed was filtered, washed with cold $H_2O$ and recrystallized from methanol, mp. 193°–96°; yield 1.5g (55%); λ max mµ (ε) 240 (28,600), 306 (5,750); ν max 740 (m), 800 (m), 980 (m), 1060 (m), 1195 (m), 1280 (m), 1580 (s), 1615 (m), 1630 (m), 1745 (ms) cm$^{-1}$.

Anal. Calcd. for $C_{14}H_{12}O_5$: C, 64.61; H, 4.65. Found: C, 64.61; H, 4.91.

EXAMPLE 3

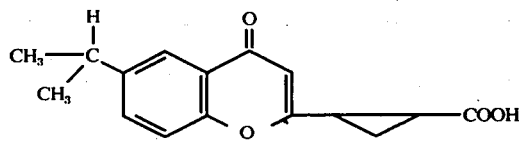

2-[6-(1-methylethyl)-4-oxo-4H-1-benzopyran-2-yl]cyclopropanecarboxylic acid

A mixture of 5.5g of ethyl 2-[6-(1-methylethyl)-4-oxo-4H-1-benzopyran-2-yl]cyclopropane carboxylate and 125ml of concentrated HCl was refluxed for 1 hr. The solution was then diluted to 250ml with ice-$H_2O$, and the precipitate that formed was filtered, washed with cold $H_2O$ and recrystallized from $CH_3CN$, mp. 170.5°–71.5°; yield 3g (70%); λ max mµ (ε) 236 (27,200), 272 (12,100), 300 (7,600); ν max 830 (ms), 975 (m), 1230 (ms), 1615 (m), 1660 (s), 1695 (s) cm$^{-1}$.

Anal. Calcd. for $C_{16}H_{16}O_4$: C, 70.57; H, 5.92. Found: C, 70.40; H, 5.86.

EXAMPLE 4

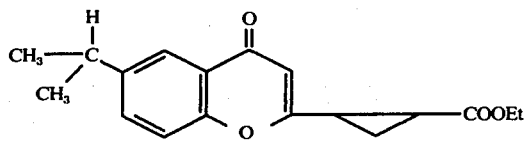

Ethyl 2-[6-(1-methylethyl)-4-oxo-4H-1-benzopyran-2-yl]cyclopropane carboxylate

A mixture of 12g of 2'-hydroxy-6'-isopropyl-2-(methylsulfinyl)acetophenone, 7.1g of ethyl 2-formyl-1-cyclopropane carboxylate (Aldrich Chem. Co.), 250ml of toluene and 0.5ml of piperidine was refluxed for 8 hrs. The toluene was then removed under reduced pressure, and the oily residue was recrystallized from skelly B, mp. 82°–83°; yield 8g (53%); λ max mµ (ε) 235 (27,100), 272 (11,600), 302 (7,000); ν max 830 (ms), 1180 (s), 1640 (s), 1660 (s), 1730 (s) cm$^{-1}$.

Anal. Calcd. for $C_{18}H_{20}O_4$: C, 71.98; H, 6.71. Found: C, 72.09; H, 6.65.

EXAMPLE 5

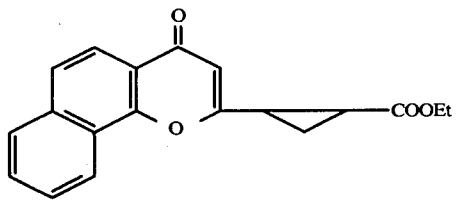

Ethyl 2-(4-oxo-4H-naphtho[1,2-b]pyran-2-yl)cyclopropane carboxylate

A mixture of 12.4g of 1'-hydroxy-2-(methylsulfinyl)-2'-acetonaphthone, 7.1g of ethyl 2-formyl-1-cyclopropane carboxylate, 250ml of toluene and 0.5ml of piperidine was refluxed for 8 hrs. The toluene was then removed under reduced pressure, and the oily residue was recrystallized from Skelly B with the aid of charcoal, mp. 106°–07.5°; yield 6.5g (42%); λ max mµ (ε) 219 (50,000), 259 (36,800), 327 (3,990), 341 (4,100); ν max 760 (m), 825 (ms), 1195 (s), 1640 (s), 1650 (s), 1730 (s) cm$^{-1}$.

Anal. Calcd. for $C_{19}H_{16}O_4$: C, 74.01; H, 5.23. Found: C, 74.17; H, 5.33.

EXAMPLE 6

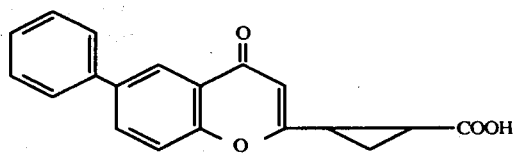

2-(4-oxo-6-phenyl-4H-1-benzopyran-2-yl)cyclopropane carboxylic acid

A mixture of 6.5g of ethyl 2-(4-oxo-6-phenyl-4H-1-benzopyran-2-yl) cyclopropane carboxylate and 125ml of concentrated HCl was refluxed for 1 hour. The mixture was chilled, and the precipitate filtered, washed with cold $H_2O$, and recrystallized from $CH_3CN$, mp. 226°–27.5°; yield 4.5g (75%); λ max mµ (ε) 254 (48,500); 309 (5,050); ν max 765 (m), 985 (m), 1210 (ms), 1595 (ms), 1630 (s), 1740 (ms)cm$^{-1}$.

Anal. Calcd. for $C_{19}H_{14}O_4$: C, 74.50; H, 4.61. Found: C, 74.26; H, 4.60.

EXAMPLE 7

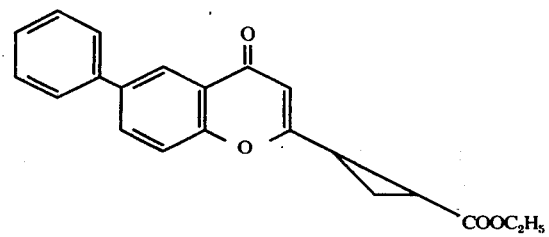

Ethyl 2-(4-oxo-6-phenyl-4H-1-benzopyran-2-yl)cyclopropane carboxylate

A mixture of 13.7g of 2'-hydroxy-2-(methylsulfinyl)-6'-phenyl acetophenone, 7.1g of ethyl 2-formyl-1-cyclopropane carboxylate, 250ml of toluene and 0.5ml of piperidine was refluxed for 8 hrs. The toluene was then removed under reduced pressure, and the semicrystalline residue recrystallized from absolute ethanol, mp. 134°–41°; yield 10g (60%); λ max mμ (ε) 253 (48,200), 313 (4,700); ν max 770 (m), 1190 (m), 1650 (s), 1725 (ms) cm$^{-1}$.

Anal. Calcd. for $C_{21}H_{18}O_4$: C, 75.43; H, 5.43. Found: C, 74.25; H, 5.57.

EXAMPLE 8

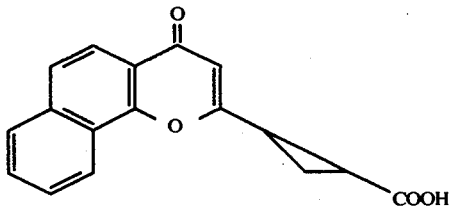

2-(4-oxo-4H-naphtho[1,2-b]pyran-2-yl)cyclopropane carboxylic acid

A mixture of 3g of ethyl 2-(4-oxo-4H-naphtho[1,2-b]pyran-2-yl)cyclopropane carboxylic acid and 50ml of concentrated HCl was refluxed for 1 hr. The mixture was chilled, and the precipitate was filtered, washed with cold $H_2O$, and recrystallized from DMF, mp. 286°–88°; yield 1.5g (55%); λ max mμ (ε) 219 (45,500); 258 (36,600), 325 (3,600), 340 (4,300); ν max 760 (ms), 875 (m), 915 (m), 1000 (m), 1175 (s), 1570 (ms), 1595 (s), 1645 (s), 1730 (s) cm$^{-1}$.

Anal. Calcd. for $C_{17}H_{12}O_4$: C, 72.85; H, 4.32. Found: C, 72.66; H, 4.33.

We claim:
1. A compound of the formula:

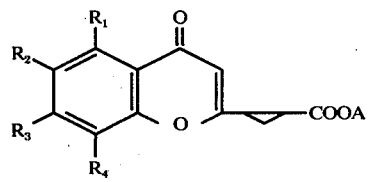

wherein $R_1$, $R_2$, $R_3$ and $R_4$ are hydrogen, lower alkyl of 1–7 carbon atoms, lower alkoxy of 1–7 carbon atoms, or phenyl, and A is hydrogen or ethyl.

2. A compound according to claim 1 which is ethyl 2-(8-methoxy-4-oxo-4H-1-benzopyran-2-yl)cyclopropane carboxylate.

3. A compound according to claim 1 which is 2(8-methoxy-4-oxo-4H-1-benzopyran-2-yl)cyclopropane carboxylic acid.

4. A compound according to claim 1 which is 2-[6-(1-methylethyl)-4-oxo-4H-1-benzopyran-2-yl]cyclopropanecarboxylic acid.

5. A compound according to claim 1 which is ethyl 2-[6-(1-methylethyl)-4-oxo-4H-1-benzopyran-2-yl]cyclopropane carboxylate.

6. A compound according to claim 1 which is 2-(4-oxo-6-phenyl-4H-1-benzopyran-2-yl)cyclopropane carboxylic acid.

7. A compound according to claim 1 which is ethyl 2-(4-oxo-6-phenyl-4H-1-benzopyran-2-yl)cyclopropane carboxylate.

* * * * *